United States Patent [19]

Robicsek

[11] Patent Number: 4,964,849
[45] Date of Patent: Oct. 23, 1990

[54] TWO-WAY SUCTION APPARATUS FOR SURGICAL PROCEDURES

[76] Inventor: Francis Robicsek, 1960 Randolph Rd., Charlotte, N.C. 28207

[21] Appl. No.: 816,562

[22] Filed: Jan. 6, 1986

[51] Int. Cl.$^5$ .............................................. A61M 1/00
[52] U.S. Cl. ........................................ 604/35; 604/33; 604/902; 604/119
[58] Field of Search ................... 128/DIG. 3, 205.24; 137/625.48; 604/4–6, 27, 32–35, 119–121, 902, 48

[56] References Cited

U.S. PATENT DOCUMENTS

| | | | |
|---|---|---|---|
| 2,796,887 | 6/1957 | Stein | 137/625.48 |
| 4,006,745 | 2/1977 | Sorenson et al. | 604/4 |
| 4,062,360 | 12/1977 | Bentley | 128/DIG. 3 |
| 4,411,786 | 10/1983 | Russell | 604/5 |
| 4,416,658 | 11/1983 | Numazawa et al. | 604/902 |
| 4,526,573 | 7/1985 | Lester et al. | 604/33 |

Primary Examiner—J. L. Kruter
Attorney, Agent, or Firm—Shefte, Pinckney & Sawyer

[57] ABSTRACT

A self-contained two-way suction device for use in surgical operations provides a suction nozzle and a two-way valve selectively determining communication between the nozzle and two parallel exhaust tubes for selectively providing return suction of shed blood to a heart-lung machine or other blood saver device and discard suction of saline solution or the like to a discharge location or cell washing system.

7 Claims, 1 Drawing Sheet

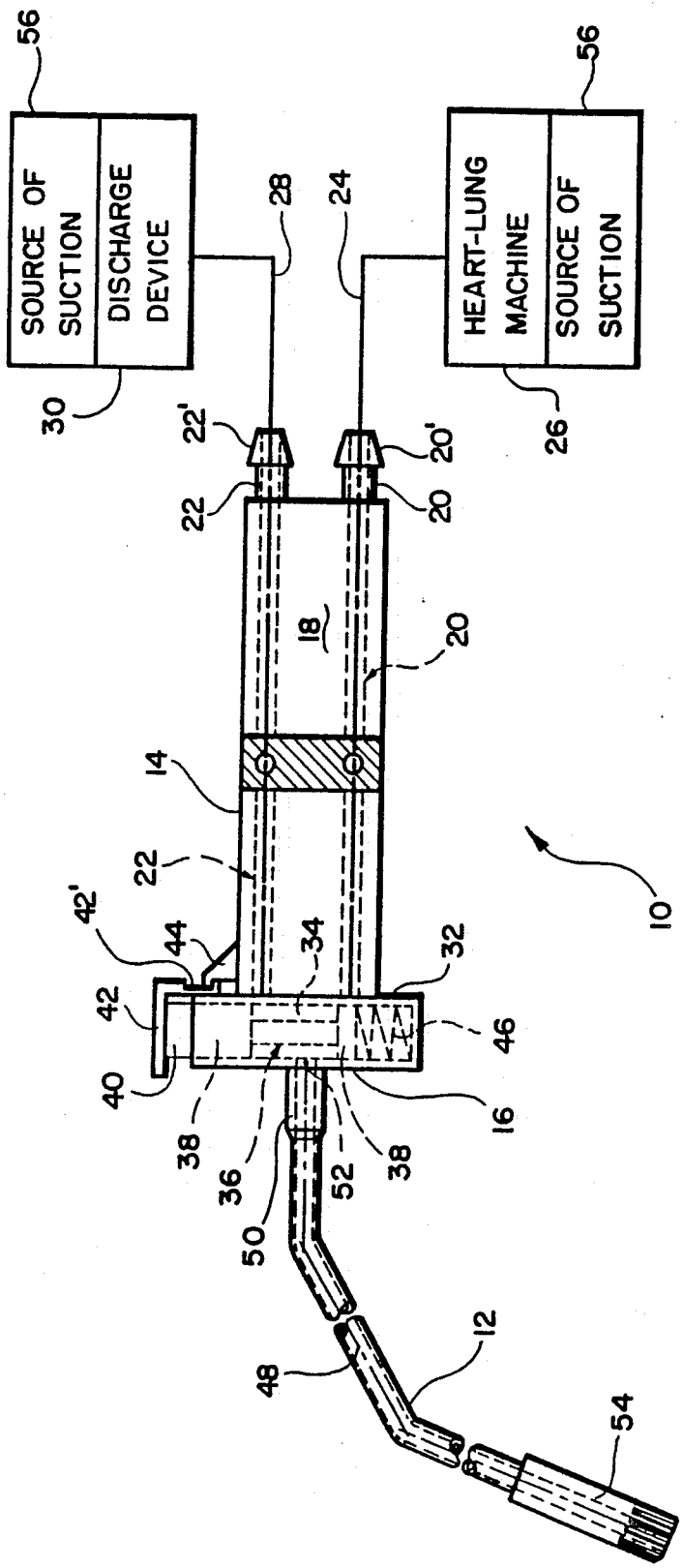

TWO-WAY SUCTION APPARATUS FOR SURGICAL PROCEDURES

BACKGROUND OF THE INVENTION

During open heart and similar surgical procedures, several suction systems are often utilized at the operating table for withdrawing materials from the surgical area. For example, so-called "return" suction systems communicate with a blood saver device, such as a heart-lung machine in open heart surgical procedures, for retrieving blood shed during the surgery. Other suction systems are used to remove saline solutions in which the surgical area is bathed for cooling purposes, such suction systems communicating with a discharge location to discard the suctioned saline solution. The use of these two suction systems on the operating table during a surgical procedure often becomes cumbersome and confusing. Furthermore, the return suction systems are conventionally operated to provide continuous suction through the return system which serves to continuously draw ambient air from the operating room through the blood saver device, heart-lung machine or the like, thereby posing a risk of breaching the sterility thereof.

The present invention overcomes these problems of conventional suction systems by providing a self-contained two-way suction system providing both return suction and discard suction capabilities.

SUMMARY OF THE INVENTION

Briefly summarized, the present invention provides a two-way suction apparatus for use in open heart surgical procedures and the like, which includes a nozzle device adapted to be selectively manipulated and applied to a surgical area, an exhaust device defining first and second parallel exhaust pathways which communicate respectively with separate deposit locations, and a two-way valve assembly intermediate the nozzle device and the exhaust device for selectively controlling communication between the nozzle device and one or the other of the first and second exhaust pathways. A source of suction is applied to each of the first and second exhaust pathways. In this manner, selective operation of the valve assembly permits suction flow from the surgical area to be directed into and through the nozzle device and the actively communicative one of the exhaust pathways to deliver suctioned material from the surgical area to the respective deposit location.

Preferably, the first exhaust pathway communicates with a blood saver device for recirculation of suctioned material withdrawn from the surgical area and the second exhaust pathway communicates with a discharge device for discarding of the suctioned material withdrawn from the surgical area. Alternatively, if so desired, the first exhaust pathway may be directed to the pump-oxygenator of a heart-lung machine and the second exhaust pathway may be directed to a blood washing (cell saver) machine. The valve assembly is biased to normally maintain communication between the nozzle device and the second exhaust pathway so that, while the suction apparatus is not in use for return purpose, ambient air from the operating room is not directed into the blood saver device, substantially reducing the risk of breaching the sterility thereof. In the preferred embodiment, the valve assembly includes an operating button arrangement for convenient manual operation of the valve assembly. The exhaust device includes a longitudinal housing compactly containing the first and second exhaust pathways therethrough in essentially parallel relation.

BRIEF DESCRIPTION OF THE DRAWING

The drawing FIGURE is a partially schematic and partially side elevational view of the suction apparatus of the invention.

DESCRIPTION OF THE PREFERRED EMBODIMENT

Referring now to the accompanying drawing, the two-way suction apparatus of the present invention is indicated generally at 10 and basically includes a nozzle device 12, an exhaust device 14 and a two-way valve assembly 16 intermediate the nozzle and exhaust devices 12,14.

The exhaust device 14 includes a longitudinal housing 18 through which extend a pair of exhaust tubes 20,22 in substantially parallel relation, the exhaust tubes 20,22 extending outwardly from the discharge end of the exhaust device 14 and respectively terminating in connector nipples 20', 22'. The connector nipple 20' of the first exhaust tube 20 is connected through an appropriate tubular or similar conduit schematically indicated at 24 with a conventional so-called "blood saver device" 26 which may be heart-lung machine or other device or apparatus adapted for retrieval of blood shed during a surgical procedure. The connector nipple 22' of the second exhaust tube 22 is similarly connected through a tubular or like conduit 28 with a discharge device or location which may provide simply for discard of the suctioned material or may include a blood washing (cell saver) machine. Each of the blood saver device 26 and the discharge device 30 includes a source of suction to be applied through their respectively associated tubular conduits 24,28 and exhaust tubes 20,22.

The valve assembly 16 includes a valve housing 32 mounted to the intake end of the housing 18 transversely of the exhaust tubes 20,22, the valve housing 32 defining an interior valve chamber 34 into opposite ends of which the exhaust tubes 20,22 open. A valve spool 36 is slidably disposed within the valve chamber 34 for movement transversely of the exhaust tubes 20,22, the valve spool 36 having enlarged portions 38 at each end thereof spaced apart a predetermined distance for simultaneously closing the opening between one or the other exhaust tubes 20,22 and the valve chamber 34 while leaving unrestricted the opening between the remaining exhaust tube 20,22 and the valve chamber 34. The valve spool 36 includes a projecting portion 40 which extends outwardly from the valve housing 32 and is fitted with a button portion 42 adapted to permit manual actuation of sliding movement of the valve spool 36. A retaining flange 42 mounted on the exterior of the housing 18 of the exhaust device 14 engages in a slot 42' in the button 42 to determine the degree of permissible sliding movement of the valve spool 36. A coil apring 46 is positioned within the valve housing 32 to resiliently bias the valve spool 36 into a normal position closing communication between the first exhaust tube 20 and the valve chamber 34 while simultaneously opening communication between the second exhaust tube 22 and the valve chamber 34.

The nozzle device 12 includes an elongated tubular member 48 having several angular bends formed therein to provide an elbow-like configuration to the tubular member 48. One end of the tubular member 48 is fitted by a connector portion 50 through an opening 52 in the valve housing 32 to provide open communication between the tubular member 48 and the central area of the valve chamber 34. A nozzle member 54 is fitted to the opposite outward free end of the tubular member 48 to be adapted for application to a surgical area for suction operation thereon.

In operation, the suction apparatus 10 is utilized in essentially the same manner as conventional suction devices to withdraw shed blood, saline solution or like materials from the surgical area as may be necessary or desirable. When it is desirable to remove saline solution or a like material from the surgical area to be discarded or to be delivered to a blood washing (cell saver) device, the valve assembly 16 is left with its valve spool 36 in its normal disposition to provide suction communication of the suction source from the discharge device 30 through its associated tubular conduit 28, the exhaust tube 22, the valve chamber 34 and the tubular member 48 to withdraw through such pathway the suctioned saline solution or other suctioned material from the surgical area to be discarded or processed at the discharge device 30. On the other hand, when it is desirable to suction away shed blood from the surgical area and to collect such shed blood for recirculation, the valve assembly 16 is operated by its button 42 to depress the valve spool 36 and thereby close communication between the exhaust tube 22 and the valve chamber 34 while simultaneously opening communication between the exhaust tube 20 and the valve chamber 34, whereby the suction source of the heart-lung machine or any other blood saver device 26 is applied through the associated tubular conduit 24, the exhaust tube 20, the valve chamber 34 and the tubular member 48 to withdraw the shed blood through such pathway and direct the blood to the blood saver device 26.

It will therefore be understood that the present suction apparatus 10 advantageously eliminates the need in surgical operations for separate return and discard suction systems, and also provides the opportunity to use two collection systems, thereby providing substantially greater convenience in use and avoiding possible confusion between the two suction systems. Furthermore, since the valve assembly 16 is constructed to normally maintain closed the defined pathway to the heart-lung machine or other blood saver device 26, ambient air from the operating room may be drawn through the suction device 10 to the heart-lung machine or blood saver device 26 only during the particular periods of time while the apparatus 10 is being used for return suction purposes and, accordingly, the sterility of the heart-lung machine or other blood saver device 26 is substantially enhanced and better maintained than with conventional suction devices.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiment, adaptations, variations, modifications and equivalent arrangements, the present invention being limited only by the claims appended hereto and the equivalents thereof.

I claim:

1. A two-way suction apparatus for use in open heart surgical procedures and the like, comprising nozzle means adapted to be selectively manipulated and applied to a surgical area, exhaust means defining first and second parallel exhaust pathways communicating respectively with separate deposit locations, a source of suction applied to each of said first and second exhaust pathways, and two-way valve means intermediate said nozzle means and said exhaust means for selectively controlling communication between said nozzle means and one or the other of said first and second exhaust pathways for directing suction flow from said surgical area into and thorugh said nozzle means and the actively communicative one of said exhaust pathways to its respective deposit location.

2. A two-way suction apparatus according to claim 1 and characterized further in that said first exhaust pathway communicates with a blood saver device for recirculation of suctioned material withdrawn from said surgical area and said second exhaust pathway communicates with a discharge device for discarding of suctioned material withdrawn from said surgical area, said valve means being biased to normally maintain said nozzle means in communication with said second exhaust pathway.

3. A two-way suction apparatus according to claim 1 and characterized further in that said first exhaust pathway communicates with a blood saver device for recirculation of suctioned material withdrawn from said surgical area and said second exhaust pathway communicates with a blood washing device for processing the suctioned material withdrawn from said surgical area, said valve means being biased to normally maintain said nozzle means in communication with said second exhaust pathway.

4. A two-way suction apparatus according to claim 1 and characterized further in that said exhaust means includes a longitudinal housing compactly containing said first and second exhaust pathways therethrough in essentially parallel relation.

5. A two-way suction apparatus according to claim 1 and characterized further in that said valve means includes button means for manual operation of said valve means.

6. A two-way suction apparatus according to claim 2 and characterized further in that said valve means includes button means for manual operation of said valve means.

7. A two-way suction apparatus according to claim 3 and characterized further in that said valve means includes button means for manual operation of said valve means.

* * * * *

UNITED STATES PATENT AND TRADEMARK OFFICE
CERTIFICATE OF CORRECTION

PATENT NO. : 4,964,849

DATED : October 23, 1990

INVENTOR(S) : Francis Robicsek

It is certified that error appears in the above-identified patent and that said Letters Patent is hereby corrected as shown below:

Column 1, Line 61, reads "return purpose," but should read -- return suction purposes, --.

Column 2, Line 7, after "of the" add -- present --.

Column 2, Line 26, after "be" add -- a --.

Column 2, Line 58, reads "apring" but should read -- spring --.

Column 4, Line 24, reads "thorugh" but should read -- through --.

Signed and Sealed this

Seventeenth Day of November, 1992

*Attest:*

DOUGLAS B. COMER

*Attesting Officer*   *Acting Commissioner of Patents and Trademarks*